United States Patent [19]

Weber et al.

[11] 4,377,801
[45] Mar. 22, 1983

[54] OXYGEN SENSOR FOR DETECTING THE OXYGEN CONTENT OF AN INTERNAL COMBUSTION ENGINE EXHAUST GAS SYSTEM

[75] Inventors: David C. Weber, Toledo; Alan H. Bilger; Philip R. Woodruff, both of Tiffen, all of Ohio

[73] Assignee: Bendix Autolite Corporation, Fostoria, Ohio

[21] Appl. No.: 311,685

[22] Filed: Oct. 15, 1981

[51] Int. Cl.³ .............................................. H01L 7/00
[52] U.S. Cl. ...................................... 338/34; 73/27 R
[58] Field of Search .................... 338/34; 73/27 R; 324/71 R, 71 SN; 23/232 E; 422/98

[56] References Cited

U.S. PATENT DOCUMENTS 4,007,435  2/1977  Tien .................................. 338/34 X
4,147,513  4/1979  Bienkowski et al. ............. 23/232 E
4,225,842  9/1980  Schlesselman et al. ............. 338/34

Primary Examiner—C. L. Albritton
Attorney, Agent, or Firm—Leo H. McCormick, Jr.; Ken C. Decker

[57] ABSTRACT

An oxygen sensor (1) for detecting the oxygen content of an internal combustion engine exhaust gas system includes a generally cylindrical hollow insulator (3) having a first resistive element (17), preferably of titania, and a second resistive element (19) preferably of zirconia or chromia, adjacent the closed end (9) thereof, grooves (23) adjacent the open end (7) thereof, and an intermediate portion (11) having a shoulder (13), with electrically conductive film leads (29) passing over the surface of the insulator (3) between the resistive elements (17 and 19) and the grooves (23), with a dielectric coating (33) over the conductive film leads (29) in the area of a metal shell (31) to insulate the film leads (29) from the shell (31).

10 Claims, 4 Drawing Figures

OXYGEN SENSOR FOR DETECTING THE OXYGEN CONTENT OF AN INTERNAL COMBUSTION ENGINE EXHAUST GAS SYSTEM

This invention relates to oxygen sensors and more particularly to resistive-type oxygen sensors for detecting the oxygen content of an internal combustion engine exhaust gas system.

Oxygen sensors are known which use the change in resistivity of a metal oxide, such as titanium dioxide, at a given temperature as a function of the partial pressure of oxygen in a gaseous atmosphere, to measure the oxygen content of that gaseous atmosphere. In order to compensate for the resistance change of such a titanium oxide relative to a change in temperature, the use of a thermistor or compensator such as zirconium oxide, which has a resistance change only as a function of temperature, has been proposed. With the use of such a thermistor, the titanium dioxide sensor can be compensated for temperature variations by exposing both the titanium dioxide element and the zirconium dioxide element to the gaseous atmosphere and electrically cancelling the change in resistance due to temperature in the manner taught by U.S. Pat. No. 4,147,513, dated Apr. 3, 1979 and entitled "Method and Apparatus for Measuring the $O_2$ Content of a Gas", the contents of which are incorporated by reference herein. It has also been proposed to use a chromium oxide compensator, which chromium oxide varies negatively, relative to titanium dioxide, as a function of the oxygen in a gaseous mixture.

One type of such an oxygen sensor is described in U.S. Pat. No. 4,007,435, dated Feb. 8, 1977 and entitled "Sensor Device and Method of Manufacturing Same", where an electrically insulative ceramic element has on the surface a layer of oxygen sensing metal oxide, such as titania, and a layer of thermistor material, with a layer of electrical resistance heating material separated therefrom by insulative ceramic. The sensor is of rectangular design formed of plates. Such a rectangular design is less durable than a cylindrical design and requires a number of process steps in manufacture. In the oxygen sensor described in U.S. Pat. No. 4,147,513, referred to above, a unitary, cylindrical ceramic insulator is described having a recess in one end thereof, wherein titania and zirconia resistors are located, with platinum wire leads extending through three bores in the insulator and through axial bores in terminals which are cemented in counterbores in the opposite end of the insulator. While this sensor is satisfactory in performance, it requires numerous manufacturing steps for its manufacture, is difficult to assemble and the long lengths of platimium wire for the leads incurs added expense. In a more recent design described in U.S. Pat. No. 4,225,842, dated Sept. 30, 1980 and entitled "Resistance Type Oxygen Sensor", a cylindrical design of resistive, compensated sensor is provided that is formed of two cylindrical insulator sections with axial bores therethrough for passage of wire leads from the titania and zirconia elements to spaced terminals. This construction provides more durability due to its cylindrical structure relative to rectangular plated structure but still requires a plurality of ceramic insulators, a number of process steps and expensive platinum wire leads. Accordingly, a need exists for a cylindrical ceramic resistive type oxygen sensor that is easily manufactured and economical in design.

DISCLOSURE OF THE INVENTION

This invention provides an oxygen sensor for detecting the oxygen content of an internal combustion engine exhaust gas system that is formed from a single cylindrical ceramic element and is readily constructed. The invention is characterized by a generally cylindrical hollow insulator having an open end, a closed end, and an intermediate portion with a shoulder formed thereabout. There are provided a first resistive element, such as titania, and a second resistive element, such as zirconia or chromia, on the surface of the insulator adjacent the closed end, and grooves in the insulator adjacent the open end and communicating therewith, with electrically conductive film leads passing over the surface of the insulator and the shoulder thereof from the resistive elements to the grooves. A metal shell is provided about the intermediate portion with a dielectric coating over the film leads in the area of the shell to insulate the film leads from the shell.

Accordingly, it is an advantage of this invention to provide a resistive-type oxygen sensor that is readily produced from a cylindrical insulator such that reduced cost in forming the sensor is achieved.

Another advantage is that a resistive-type oxygen sensor is provided that has the strength and stability of a cylindrical unit and is easily mounted in the exhaust gas system of an internal combustion engine.

DETAILED DESCRIPTION OF THE INVENTION

Figure 1:
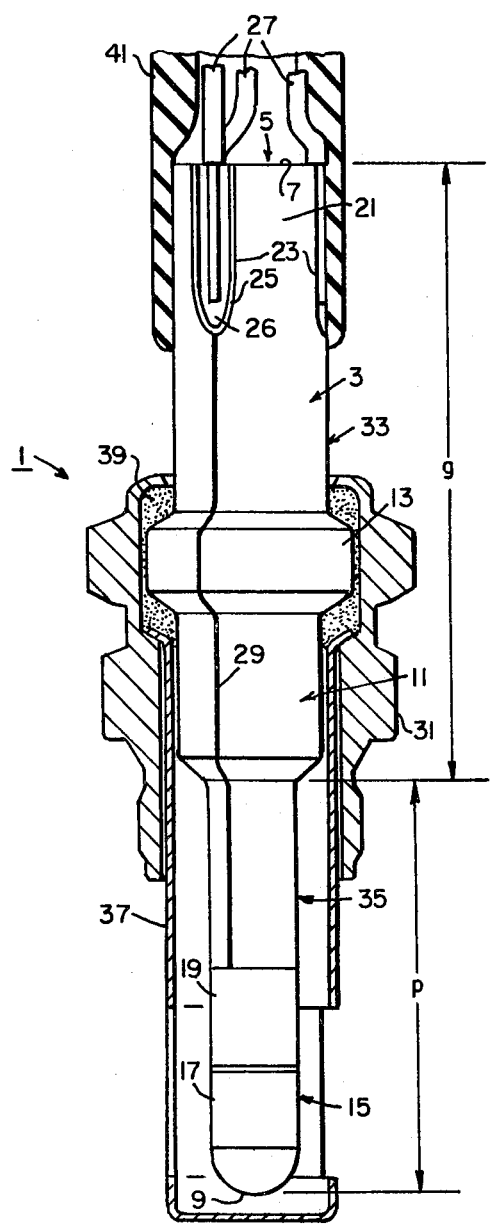
FIG. 1 is a view, partially in cross-section, of a resistive-type oxygen sensor incorporating the principles of of the present invention.

Referring now to the drawings, FIG. 1 illustrates a resistance-type oxygen sensor 1 embodying the principles of the present invention. The resistance-type oxygen sensor 1 is formed from a generally cylindrical hollow electrical insulator 3 of ceramic material, such as alumina or cordierite, having a bore 5, with the insulator having an open end 7, a closed end 9, and an intermediate portion 11. Formed about the intermediate portion 11 of the insulator 3 is a raised shoulder 13. The insulator 3 may be readily fabricated by isostatic pressing of a ceramic powder. Any ceramic material having good thermal shock resistance, high electrical resistance, good mechanical strength and a hermetic seal may be used in fabricating the insulator 3, which preferably has a thin wall at its closed end and a thicker wall at its open end.

Positioned on the lower outer surface 15 of the insulator 3 adjacent the closed end 9 thereof are a film of a first resistive element 17 formed of a metal oxide having electrical resistance characteristics that vary as a function of both temperature and the presence of oxygen in a gaseous atmosphere to which it is exposed, and a second resistive element 19 formed of a metal oxide having an electrical resistance characteristic that varies as a function of the temperature of the gaseous atmosphere to which it is exposed in a manner similar to that of the first resistive element, and either varies negatively or does not vary as a function of the oxygen present in the gaseous atmosphere. Preferably, the first resistive element is comprised of titanium dioxide, while the second resistive element is comprised of zirconium dioxide or chromium oxide. These resistive elements may be readily applied by spraying, painting, screen printing, transfer printing, tape transfer or other means.

At the opposite or open end 5 of the electrical insulator 3, there are formed in the upper outer surface 21 thereof a plurality of axial grooves 23.

Figure 2:
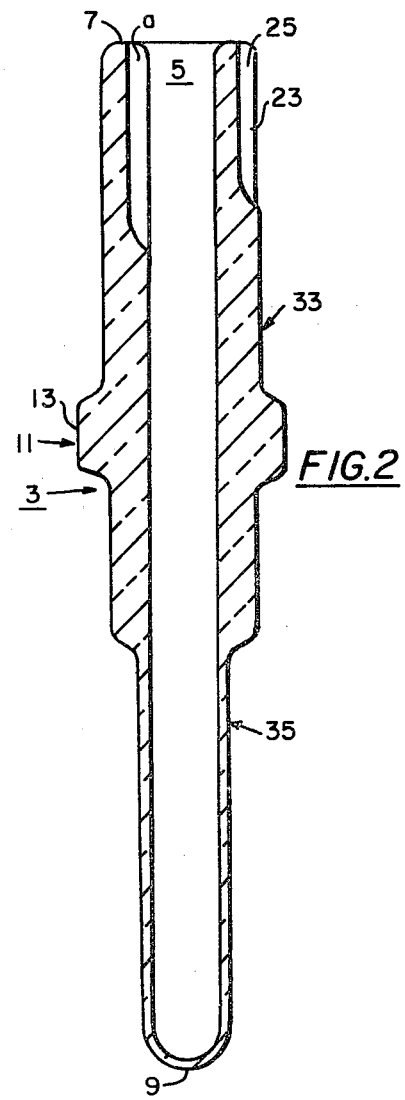
FIG. 2 is a cross-sectional view of a generally cylindrical hollow insulator of the oxygen sensor incorporating the principals of the present invention.

FIG. 2 illustrates a cross-section of the hollow insulator 3 of the sensor of FIG. 1, showing a groove a on the inner surface of the insulator 3, adjacent the open end 7, which is provided as a locating groove for easy alignment of the insulator 3 during fabrication and assembly of the sensor components.

Figure 3:
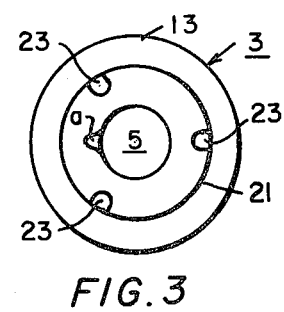
FIG. 3 is an end view of the generally cylindrical hollow insulator illustrated in FIG. 2.

As illustrated in FIG. 3, the axial grooves 23 are formed in the upper outer surface 21 adjacent the open end 5 of the electrical insulator and communicate with the end thereof. The grooves have a conductive layer 25, such as a film of silver or silver-palladium ink, therein to provide a sure contact between the conductive film means described hereinafter and lead wires 27 that extend from the sensor by means of a conductive connection 26, which may be solder, braze, organic glue, spring contact, weld, or other connection.

In order to provide an electrical conductive path between the sensing elements 17 and 19 adjacent the closed end 9 of the insulator to the lead wires 27 in grooves 23 at the open end 7 of the insulator, electrically conductive film means 29 (e.g. platinum, silver-palladium) are provided which extend from the first and second resistive elements and over the surface of the intermediate portion 11 to the grooves.

To affix the sensor in an automotive exhaust system, a threaded metal shell 31 is used, which may be threaded into a threaded orifice in the wall of the exhaust system. In order to protect the electrically conductive film means 29 from contact with the metal shell 31, a dielectric coating 33 is applied over the film means 29 and the surface of the insulator 3 in the area of the shell. The dielectric coating 33 must cover the conductive film means 29 in the area of the metal shell 31, with the coating over the shoulder 13 of the insulator 3, and preferably the dielectric coating extends from the limit of the shoulder opposite the open end 7 of the insulator 3 to the open end, as illustrated by g in FIG. 1. The grooves 23 are however shielded so as to not be covered by the coating, and the layer 25 may thus be applied to the grooves prior to or following the application of the dielectric coating. The dielectric coating 33 may comprise glaze of a glass frit which is fired on at relatively low temperatures, or another dielectric material such as alumina, or the like.

Also, in order to protect the resistive sensing elements 17 and 19 from the harsh conditions to which they are exposed during operation of the sensor, a porous protective coating 35 is formed over the closed end of the insulator and extends to the shoulder of the intermediate portion thereof. The porous protective coating 35 covers the conductive film means 29 and first and second resistive elements 17 and 19 adjacent the closed end 9 of the insulator 3, as illustrated in FIG. 1. The porous protective coating 35 extends the distance p, from the limit of dielectric coating g to the closed end 9 and preferably encapsulates that closed end. The porous protective coating 35 may comprise known such coatings, such as spinel, or preferably, a mixture of alumina and a glass frit in a seventy-five to twenty-five weight ratio.

In the final assembly of the oxygen sensor, a protective apertured shield 37 is provided to enclose the closed end of the insulator while cushioning washers 39 (talc, copper, or the like) are used to seal the insulator within the metal shell 31, and a dielectric and watertight protective boot, or coating, 41 is placed over the open end of the insulator to encapsulate the lead wires 27.

Figure 4:
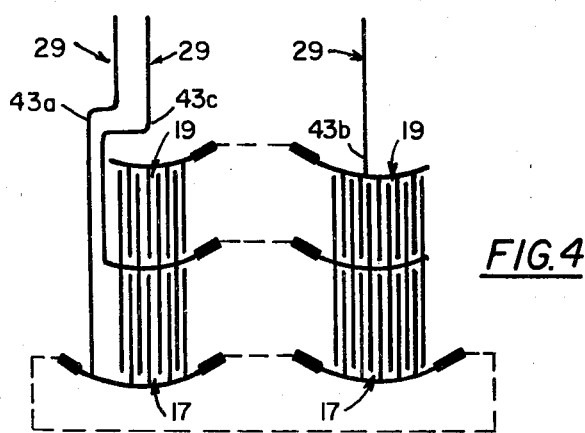
FIG. 4 is a schematic view of the preferred pattern of conductive leads adjacent the closed end of insulator of the oxygen sensor incorporating the principals of the present invention.

The sensing elements 17 and 19 are superimposed over or under a printed pattern of conductive leads 43 which connect with conductive film means 29 as illustrated in FIG. 4. As shown, a pattern of conductive leads 43a, 43b and 43c are applied to the surface of the conductor adjacent the closed end thereof. Conductive lead 43a has a layer of titania superimposed over branches of the lead, while conductive lead 43b has the compensator, such as zirconia, superimposed over branches of the lead. The third lead 43c is a common lead, with branches of that common lead situated on the insulator beneath both the titania and zirconia layers. The pattern 43 may or may not be made of the same material as the conductor film 29 or the groove layer 25. Unsable materials for the films 25, 29 and 43 are platinum alloys, silver alloys, palladium alloys, gold alloys, conductor ceramics, and the like.

The pattern on the right side of FIG. 4 roughly corresponds to the view of FIG. 1. The left side of FIG. 4 roughly corresponds to the view (not shown) behind FIG. 1. Each pattern corresponds to about 200 degrees around the cylindrical substrate 3. Overlap occurs which causes electrical conduction which is shown by dotted lines in FIG. 4. Many other pattern designs are possible besides that shown. If desired, a heating element (not shown) may readily be situated in the bore 5 of the insulator 3, through the open end 7, which would decrease the operational heat-up time, help stabilize outputs with gas temperature variations, allow analog measurements of high lean and of high rich gases, and possibly reduce fouling and degradation of the sensor film. Ready application of heater wires to such a heater could be made and the wires potted in place with an electrically insulating and refractory compound.

Having described the invention, what is claimed is:

1. An oxygen sensor for detecting the oxygen content of the gaseous atmosphere in an internal combustion engine exhaust gas system, having a first resistive element having an electrical resistance characteristic that varies as a function of both temperature and the presence of oxygen in said gaseous atmosphere to which the element is exposed, and a second resistive element having an electrical resistance characteristic that varies as a function of the temperature of said gaseous atmosphere to which the element is exposed in a manner similar to that of the first resistive element, and either varies negatively or does not vary as a function of the oxygen in said gaseous atmosphere, comprising:

a generally cylindrical hollow electrical insulator having an open end, a closed end, and an intermediate portion;

said first and second resistive elements being situated on the outer surface of the insulator adjacent the closed end;

a plurality of grooves in the outer surface of the insulator adjacent to and communicating with the open end;
a shoulder formed about the insulator at the intermediate portion thereof;
electrically conductive film means extending from said first and second resistive elements and over the surface of the intermediate portion to said grooves;
a threaded metal shell enclosing the intermediate portion of the insulator; and
a dielectric coating over said film means in the area of the metal shell to insulate the film means from the shell.

2. An oxygen sensor as defined in claim 1 wherein said first resistive element is comprised of a layer of titania.

3. An oxygen sensor as defined in claim 2 wherein said second resistive element is comprised of a layer of zirconia.

4. An oxygen sensor as defined in claim 2 wherein said second resistive element is comprised of a layer of chromia.

5. An oxygen sensor as defined in claim 3 or 4 wherein said generally cylindrical hollow insulator is a ceramic selected from the group consisting of alumina or cordierite.

6. An oxygen sensor as defined in claim 1 wherein three said grooves are formed in the outer surface of the insulator.

7. An oxygen sensor as defined in claim 5 wherein one said electrically conductive film means extends from said first resistive element to one of said grooves, a second electrically conductive film means extends from said second resistive element to a second of said grooves, and a third common electrically conductive film means extends from both said resistive elements to a third of said grooves.

8. An oxygen sensor as defined in claim 1 wherein said dielectric coating extends from the limit of said shoulder opposite said open end to said open end.

9. An oxygen sensor as defined in claim 8 wherein a porous protective coating is formed over the insulator extending from said dielectric coating to said closed end.

10. An oxygen sensor as defined in claim 8 wherein said threaded shell is metal and is crimped about said shoulder to enclose the same.

* * * * *